(12) United States Patent
Paek et al.

(10) Patent No.: US 8,369,931 B2
(45) Date of Patent: Feb. 5, 2013

(54) METHOD OF DETERMINING THE POSITION OF A DEEP BRAIN STIMULATION ELECTRODE

(75) Inventors: Sun Ha Paek, Seoul (KR); Yong Hoon Lim, Seoul (KR); Hyun Jae Kang, Seoul (KR); Se Ho Shin, Jeollanam-do (KR); Eun Ju Choi, Seoul (KR); Cheol Young Kim, Seoul (KR)

(73) Assignees: Cybermed, Inc., Kyunggi (KR); Seoul National University Industry Foundation, Seoul (KR)

( * ) Notice: Subject to any disclaimer, the term of this patent is extended or adjusted under 35 U.S.C. 154(b) by 216 days.

(21) Appl. No.: 12/666,181

(22) PCT Filed: Jun. 23, 2008

(86) PCT No.: PCT/KR2008/003577
§ 371 (c)(1),
(2), (4) Date: Dec. 22, 2009

(87) PCT Pub. No.: WO2009/002072
PCT Pub. Date: Dec. 31, 2008

(65) Prior Publication Data
US 2010/0324410 A1    Dec. 23, 2010

(30) Foreign Application Priority Data

Jun. 22, 2007  (KR) .................... 10-2007-0061894

(51) Int. Cl.
*A61B 5/00* (2006.01)

(52) U.S. Cl. ............ 600/424; 600/411; 600/427; 607/2; 607/116; 345/629; 382/128; 382/131; 382/291

(58) Field of Classification Search .................. 600/407, 600/410, 411, 416, 424, 427, 378, 544; 607/2, 607/115, 116; 345/418, 629; 382/128, 131, 382/291
See application file for complete search history.

(56) References Cited

U.S. PATENT DOCUMENTS

| | | | |
|---|---|---|---|
| 6,146,390 A | 11/2000 | Heilbrun et al. | |
| 6,253,109 B1 | 6/2001 | Gielen | |
| 2002/0009224 A1* | 1/2002 | Gatti et al. | ..................... 382/154 |
| 2004/0049121 A1 | 3/2004 | Yaron | |
| 2005/0004617 A1 | 1/2005 | Dawant et al. | |
| 2006/0017749 A1 | 1/2006 | McIntyre et al. | |
| 2009/0118610 A1* | 5/2009 | Karmarkar et al. | ........... 600/420 |

FOREIGN PATENT DOCUMENTS

WO    WO2007/064739    6/2007

* cited by examiner

*Primary Examiner* — Ruth S Smith
(74) *Attorney, Agent, or Firm* — Samuel Digirolamo; Husch Blackwell LLP (57) ABSTRACT

The present invention relates to a method of determining the position of a deep brain stimulation (DBS) electrode which finds the position of the DBS electrode with respect to a deep brain target region, by using a first volume data set containing information on the deep brain target region and a second volume data set containing information on the DBS electrode implanted toward the deep brain target region, and which includes: a first step of generating a subvolume of the deep brain target region from the first volume data set, and also generating a subvolume of the DBS electrode from the second volume data set; and a second step of overlapping and displaying the subvolume of the deep brain target region and the subvolume of the DBS electrode.

8 Claims, 10 Drawing Sheets

FIG. 1

(PRIOR ART)

FIG. 2

(PRIOR ART)

METHOD OF DETERMINING THE POSITION OF A DEEP BRAIN STIMULATION ELECTRODE

CROSS REFERENCE TO RELATED APPLICATIONS

This application is a U.S. National Phase Application of International Application PCT Application No. PCT/KR2008/003577 filed on 23 Jun. 2008, which claims the benefit of priority from Korean Patent Application No. 10-2007-0061894 filed on 22 Jun. 2007. The disclosures of International Application PCT Application No. PCT/KR2008/003577 and Korean Patent Application No. 10-2007-0061894 are incorporated herein by reference.

TECHNICAL FIELD

The present invention relates to a method of determining the position of a deep brain stimulation (DBS) electrode, and more particularly, to a method of finding the position of a subvolume-rendered DBS electrode with respect to a subvolume-rendered subthalamic nucleus (STN), by aligning a pre-implantation MRI volume data set and a post-implantation CT volume data set.

BACKGROUND ART

A DBS therapy treats an abnormal state of a patient by fixing an electrode to an aimed target (e.g., STN) of a deep brain and continuously applying electric stimulation thereto for a predetermined period.

Since firstly approved in 1998 by U.S. FDA, the DBS therapy has been very popular in the treatment of various brain-controlled disorders including a movement disorder. The DBS therapy has been applied to the treatment of drug induced side effects of patients suffering from essential tremor, rigidity, Parkinson's disease and tremor. In general, this therapy includes positioning a DBS electrode lead through a burr hole drilled into a skull of a patient, and applying proper stimulation signals to a physiological target through the electrode lead. The positioning which includes stereotactic neurosurgical methodology is very important in this therapy, attracts a lot of attention, and becomes a subject of research. Particularly, it is essential to find a deep brain target, continuously position an electrode lead, and efficiently apply stimulation to the target.

To find an optimum physiological target is very difficult in a DBS implantation for treating a movement disorder, particularly, in the treatment of symptoms that cannot be tested on an operating table during an implantation of an electrode lead. For example, in the case of a patient having the Parkinson's disease, postural stability and test walking are substantially impossible during an implantation of a DBS lead. It is also known that rigidity and akinesia, which are two other major symptoms of the Parkinson's disease, are difficult to quantitatively evaluate during an implantation of a DBS lead. In the meantime, intended operation targets include deep brain nuclei or sub-regions in globus pallidus internus or subthalamus. Such structures cannot be easily observed by any of the current imaging modalities, such as magnetic resonance imaging (MRI), computed tomography (CT) and positron emission tomography (PET).

Accordingly, in a conventional DBS implantation, a method wherein a target region is found by means of a kind of template for a brain structure, such as Schaltenbrand-Wahren atlas is used.

In addition, St-Jean et.al. create a 3D structure by stacking a plurality of slices by digitalizing Schaltenbrand-Wahren atlas, and register the 3D structure into a pre-DBS implantation MRI volume data set of a patient by using landmarks, thereby generating a pre-implantation MRI volume data set with the atlas 3D structure put thereon, and finding a target region according to the data set in the DBS implantation.

Recently, a target region is determined on a magnetic resonance (MR) image on the basis of anterior commissural (AC)-posterior commissural (PC) coordinates.

U.S. Pat. No. 7,167,760 gives overall explanations of the DBS therapy, and suggests a method of determining a target region before an implantation which solves the foregoing problems in the prior art.

Figure 1:
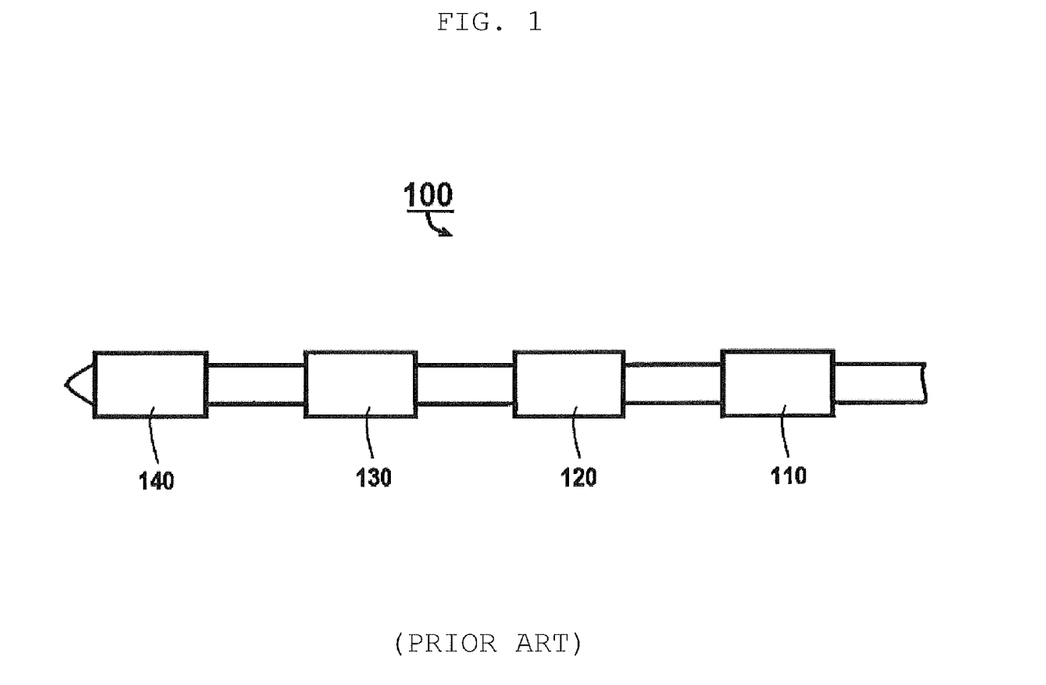
FIG. 1 is a schematic view illustrating one example of a DBS electrode lead.

FIG. 1 is a schematic view illustrating one example of a DBS electrode lead. The DBS electrode lead 100 includes four platinum/iridium contact electrodes 110, 120, 130 and 140. These electrodes 110, 120, 130 and 140 are positioned in a target region, and electric stimulation is applied to some of the electrodes 110, 120, 130 and 140 for treatment.

Figure 2:
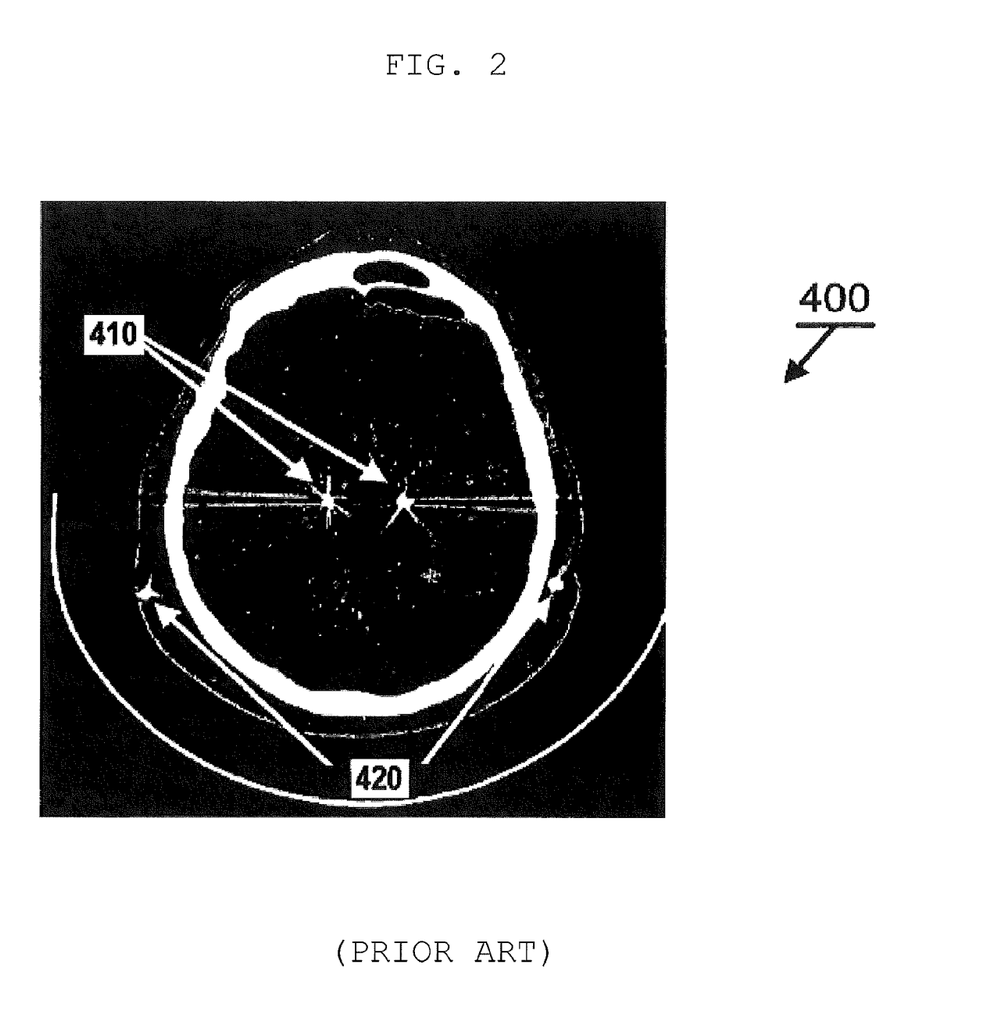
FIG. 2 is a view illustrating a CT image after an implantation of a DBS electrode.

FIG. 2 is a view illustrating one example of a CT image after an implantation of a DBS electrode, particularly, a post-implantation CT image 400 of a patient after bilateral DBS implantation using two DBS electrode leads 410. Wire leads 420 are connected from the DBS electrode leads 410 to an internal pulse generator (not shown).

Meanwhile, after the DBS electrode lead 400 or DBS electrode is implanted, or after the DBS treatment is finished, whether the DBS electrode has been normally positioned should be evaluated. In the case of using a CT image, according to characteristics of the CT, a DBS electrode is relatively easily found, but a target region which is a soft tissue is not easily found. In the case of using an MRI image, according to characteristics of the MRI, a target region which is a soft tissue is expected to be shown well. However, it is not easy to see the position relation between a DBS electrode and the target region due to an interference of the DBS electrode lead 400 or DBS electrode formed of metal.

DISCLOSURE

Technical Problem

Accordingly, the present invention has been made to solve the above-described shortcomings occurring in the prior art, and an object of the present invention is to provide a method of determining the position of a DBS electrode which can clearly find the position of the DBS electrode with respect to a target region. This method can be usefully used to determine the position of the DBS electrode with respect to the target region after an implantation of the DBS electrode. In addition, this method can be employed to position the DBS electrode with respect to the target region with the assistance of a medical navigation system during the implantation of the DBS electrode.

Another object of the present invention is to provide a method of determining the position of a DBS electrode which can clearly find the position of the DBS electrode with respect to a deep brain target region such as an STN.

A further object of the present invention is to provide a method of determining the position of a DBS electrode which can clearly find the position of the DBS electrode with respect to a target region by means of subvolume rendering of the target region and the DBS electrode.

A still further object of the present invention is to provide a method of determining the position of a DBS electrode which can clearly find the position of the DBS electrode with respect to a target region by fusing a pre-implantation volume data set and a post-implantation volume data set.

A still further object of the present invention is to provide a method of determining the position of a DBS electrode which can clearly find the position of the DBS electrode with respect to a target region by aligning a pre-implantation volume data set and a post-implantation volume data set by mutual information thereof.

A still further object of the present invention is to provide a method of determining the position of a DBS electrode which can clearly find the position of the DBS electrode with respect to a target region by aligning a pre-implantation MRI volume data set and a post-implantation CT volume data set.

Technical Solution

Hereinafter, various embodiments of the present invention will be described.

A method of determining a position of a deep brain stimulation (DBS) electrode, the method locating the position of the DBS electrode with respect to a targeted region in a deep brain of a living subject, by using a first volume data set of information on said targeted region and a second volume data set of information on said DBS electrode implanted toward said targeted region, the method comprising the steps of: generating a subvolume of the targeted region from the first volume data set of information on said targeted region, and also generating a subvolume of the DBS electrode from the second volume data set of information on said DBS electrode; and overlapping and displaying the subvolume of the targeted region and the subvolume of the DBS electrode. Here, a first volume data and a second volume data are not specially limited to MRI and CT, but can be expanded to a volume data such as PET. In addition, if necessary, this method is applicable to first and second volume data having the same modality.

Meanwhile, steps S5 and S6 can be carried out any time after step S1.

Advantageous Effects

According to a method of determining the position of the DBS electrode according to the present invention, the position of the DBS electrode with respect to a deep brain target region such as an STN can be clearly found. Finding the position is usefully used to design an implantation of the DBS electrode, implant the DBS electrode and evaluate the implantation of the DBS electrode.

Also, according to a method of determining the position of the DBS electrode, a deep brain target region can be easily identified and identification disturbance of the deep brain target region caused by the electrode can be overcome, by getting hold of the position relation between the deep brain target region and the electrode by means of image alignment between a pre-implantation volume data set and a post-implantation volume data set.

Also, according to a method of determining the position of the DBS electrode, the position relation between a deep brain target region and an electrode can be easily shown by means of a subvolume rendering technique.

Also, according to a method of determining the position of the DBS electrode, image alignment can be rapidly performed by aligning a pre-implantation volume data set and a post-implantation volume data set by mutual information thereof.

Also, according to a method of determining the position of the DBS electrode, an STN and the DBS electrode can be efficiently found and displayed by using a pre-implantation MRI volume data set and a post-implantation CT volume data set.

Also, the volume rendering technique, the image aligning technique and the subvolume rendering technique according to the present invention can be applied to a medical navigation system. In this case, the present invention can be expansively applied to a medical navigation method of a DBS electrode in an implantation of the DBS electrode.

MODE FOR INVENTION

Hereinafter, the present invention will be described in detail with reference to the accompanying drawings.

Figure 3:
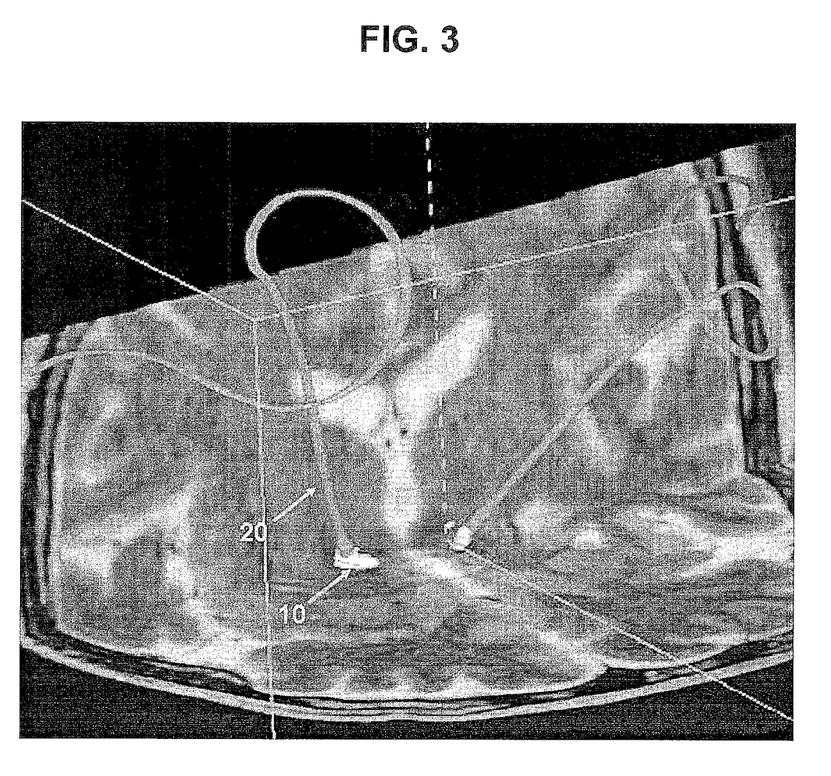
FIG. 3 is an explanatory view illustrating a method of evaluating the position relation between a target region and a DBS electrode according to the present invention.

FIG. 3 is an explanatory view illustrating a method of evaluating the position relation between a target region and a DBS electrode according to the present invention. A DBS electrode 20 is positioned on a subthalamic nucleus (STN) 10.

Figure 4:
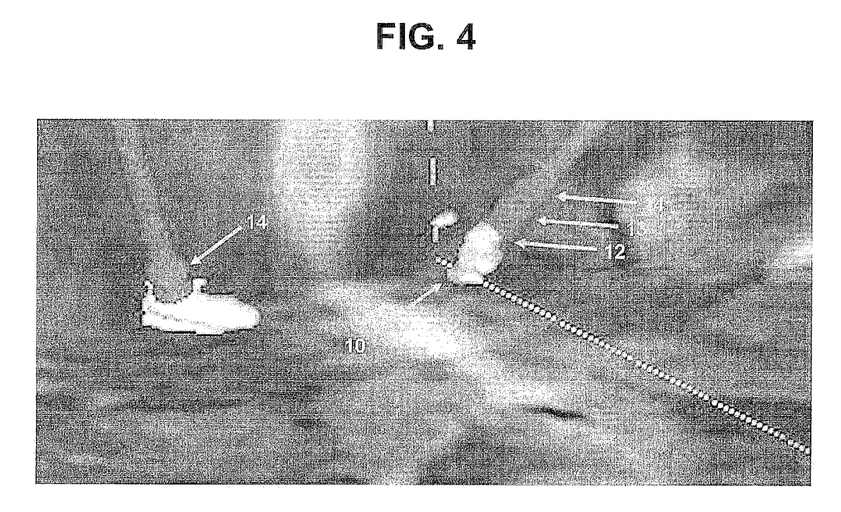
FIG. 4 is an enlarged view of FIG. 3.

FIG. 4 is an enlarged view of FIG. 3. Three exposed DBS electrodes 12, 13 and 14 are shown on a right-side STN 10. Therefore, a doctor can be informed that one of the four DBS electrodes exists within the STN 10. Since the doctor precisely knows the position of the DBS electrode with respect to the STN 10, he or she can clearly judge whether an implantation of the DBS electrode is successful, which DBS electrode needs electric stimulation, etc. to thereby reduce a treatment time of a patient. In addition, provided is the basis for precisely understanding the correlation between the electric stimulus and the target region, which has not been revealed before.

Figure 5:
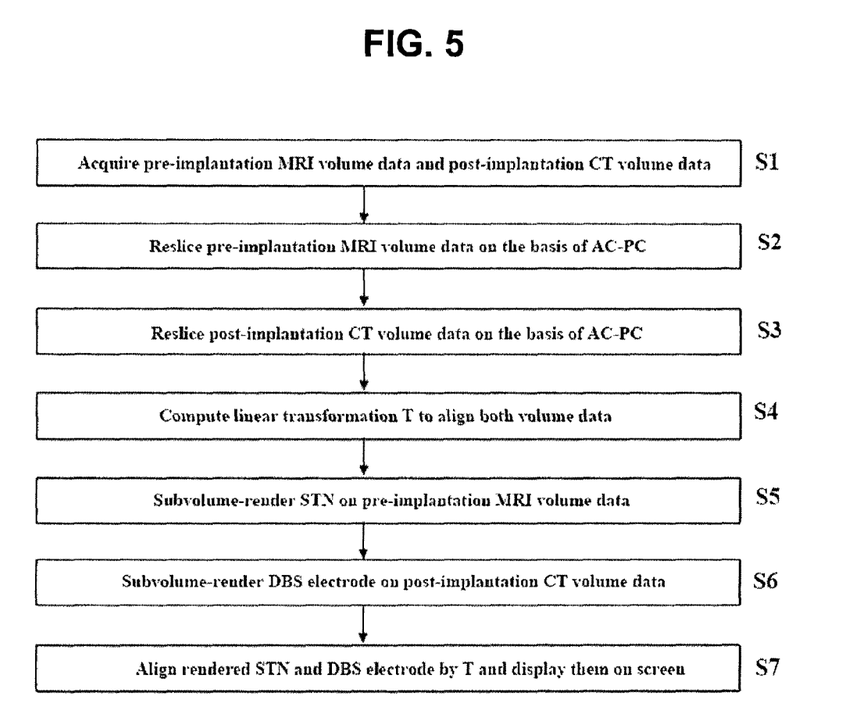
FIG. 5 is an explanatory view illustrating a method of forming an image of FIG. 3 according to the present invention.

FIG. 5 is an explanatory view illustrating a method of forming an image of FIG. 3 according to the present invention. First of all, in step S1, a pre-implantation MRI volume data set and a post-implantation CT volume data set are acquired. The pre-implantation MRI volume data set is acquired by performing MRI photographing before an implantation of a DBS electrode, and the post-implantation CT volume data set is acquired by performing CT photographing after the implantation, or after the DBS treatment of a predetermined period of time (e.g., three months, six months) from the implantation.

In step S2, a coordinate axis of the pre-implantation MRI volume data set is reset on the basis of a line connecting AC and PC which are index points in a human body. It is called reslicing. A target region (here, an STN) can be easily found by means of the reslicing (by resetting the coordinate axis).

In step S3, the post-implantation CT volume data set is resliced on the basis of the AC-PC. That is, a coordinate axis of the post-implantation CT volume data set is reset on the basis of the AC-PC, for reducing a succeeding alignment time of the pre-implantation MRI volume data set and the post-implantation CT volume data set.

In step S4, the pre-implantation MRI volume data set and the post-implantation CT volume data set having different modalities are aligned. The image alignment provides the basis for overlapping and displaying two volume data sets on one screen, and can be understood as a process of finding a linear transformation T which corresponds voxels of the post-implantation CT volume data set correspond to voxels of the pre-implantation MRI volume data set. It will be described later in more detail.

In step S5, the STN, which is a soft tissue, is rendered into a special volume data set, i.e., a subvolume on the pre-implantation MRI volume data set where the STN can be easily seen. This process is carried out by designating a corresponding intensity to the STN on the pre-implantation MRI volume data set. An atlas can be used during a process of finding the STN. The subvolume of the STN which is a hardly-identifiable deep brain soft tissue target region is generated from the pre-implantation MRI volume data set. Accordingly, the subvolume can be acquired without disturbance of the DBS electrode formed of metal.

In step S6, the DBS electrode formed of metal is rendered into a special volume data set, i.e., a subvolume on the post-implantation CT volume data set where the DBS electrode can be easily seen. This process is carried out by designating a corresponding intensity to the DBS electrode on the post-implantation CT volume data set.

In step S7, as shown in FIG. 3, the subvolume 10 of the STN acquired at step S5 and the subvolume 20 of the DBS electrode acquired at step S6 are displayed together. Here, since the subvolume 10 of the STN is generated from the pre-implantation MRI volume data set and the subvolume 20 of the DBS electrode is generated from the post-implantation CT volume data set, they need to be aligned. To this end, the linear transformation T acquired at step S4 is used.

Subvolume Rendering and Reslicing

Computer graphics is mainly used to show 2D or 3D graphic expression of an object on a 2D display screen. Volume graphics, which is one field of the computer graphics, deals with visualization of an object expressed as 3 or more dimensional sample data. Such samples are called volume elements or voxels, and contain digital information expressing physical characteristics of the object. For example, voxel data of a specific object can express density, object type, temperature, speed or another characteristic as discrete points in a space over the inside and surrounding of the object.

Recently, a volume graphics method which is called volume rendering has been introduced. The volume rendering is one type of digital signal processing, and gives colors and transparency to the respective voxels in the voxel-based expression. The respective voxels given with colors and transparency are projected on a 2D viewing surface such as a computer screen. Here, background voxels are hidden by foreground opaque voxels. The accumulation of the projected voxels results in a visual image of the object.

That is, the volume rendering is to render a volume or volume data set. The volume data set includes a 3D array of data points called volume elements or voxels. The voxel, which is a 3D equivalent to a pixel, contains color and transparency information. When the color and transparency that are data values of a specific voxel are changed, the exterior and interior of the object can be shown in different types. For example, when a doctor intends to observe a ligament, tendon and bone of a knee before an operation, he or she can display blood, skin and muscle to be completely transparent in the CT scan image of the knee.

In the meantime, before doing an operation, a doctor obtains information on the shape and position of an abnormal part (e.g., tumor) from medical images such as CT images or MRI images. Therefore, if a 3D object or volume data set created from the medical images such as the CT or MRI images can show the abnormal part to be distinguished from other tissues, it will be much more convenient. To achieve the above object, there has been suggested a multi-subvolume rendering or subvolume rendering method. Briefly, the multi-subvolume rendering displays an abnormal part (or interested part) with a different color, so that a doctor can easily judge the position and shape of the abnormal part. Currently, a volume rendering hardware solution such as VolumePro™ of TeraRecon is used to implement the multi-subvolume rendering.

Figure 6:
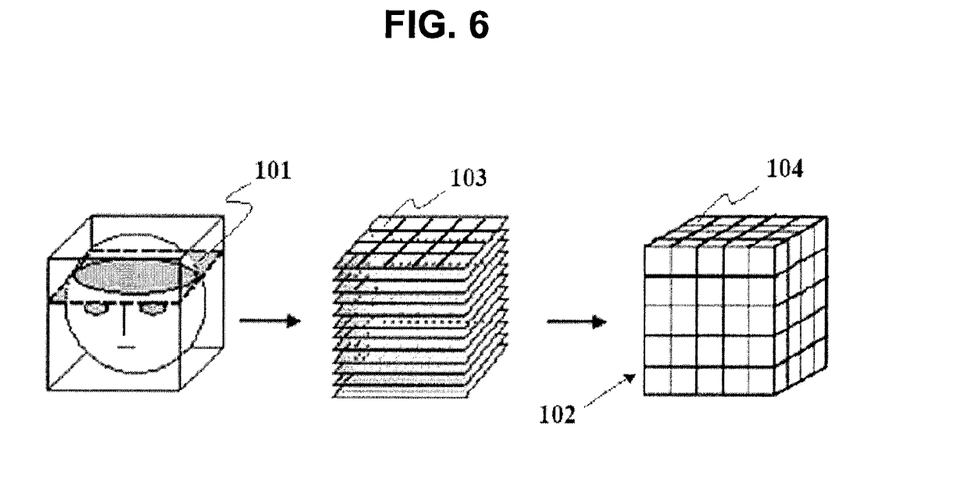
FIGS. 6 and 7 are explanatory views illustrating a subvolume rendering method.

The subvolume rendering method will be explained with reference to FIG. 6. A volume or volume data set 102 is generated from medical images 101 such as CT or MRI images photographed as many as the appropriate number. The volume or volume data set 102 can be simply considered as a stacking of several medical images 101. Pixels 103 of the respective medical images 101 correspond to voxels 104 of the volume or volume data set 102.

Each voxel 104 contains information values of color and transparency as data values.

Figure 7:
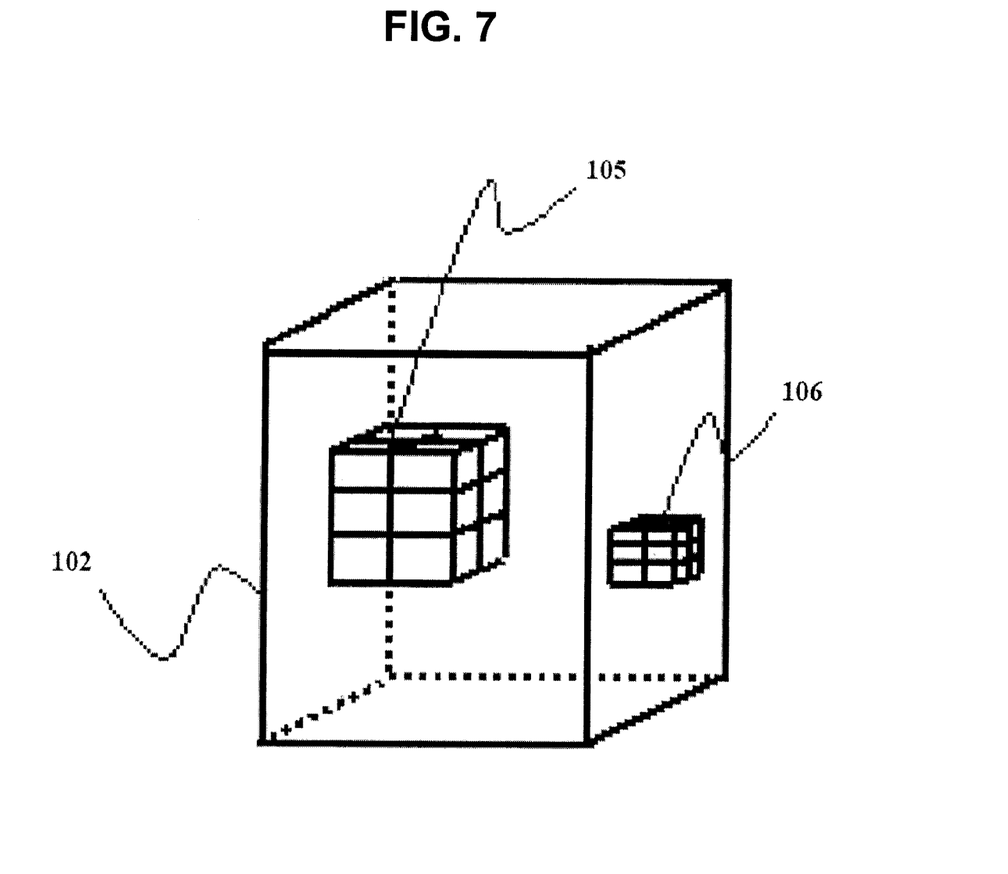

Referring to FIG. 7, according to the multi-subvolume rendering, a subvolume 105, a subvolume 106 and an entire volume 102 are individually rendered so that the subvolumes 105 and 106 can be rendered to be distinguished from the entire volume 102. Thereafter, the respective rendered images are fused. Here, rendering the subvolume 105 or the subvolume 106 individually means rendering the corresponding subvolume after setting a color suitable for the subvolume by using voxels belonging to a specific subvolume region. In terms of the entire volume, it is like obtaining a 2D image by rendering only some region (the corresponding subvolume region).

Figure 8:
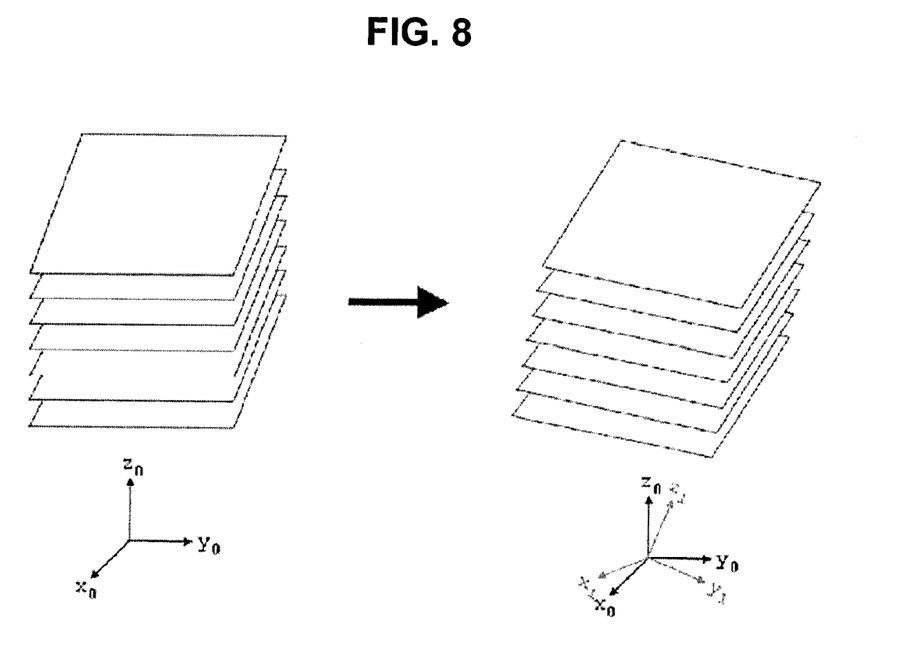
FIG. 8 is an explanatory view illustrating reslicing.

FIG. 8 is an explanatory view illustrating reslicing. The reslicing means reconstitution by re-stacking previously-stacked voxels of the left side on the basis of AC-PC. Accordingly, conceptually, the existing coordinate system ($x_0$, $y_0$ and $z_0$) is re-defined as a new coordinate system ($x_1$, $y_1$ and $z_1$).

Image Fusion

Figure 9:
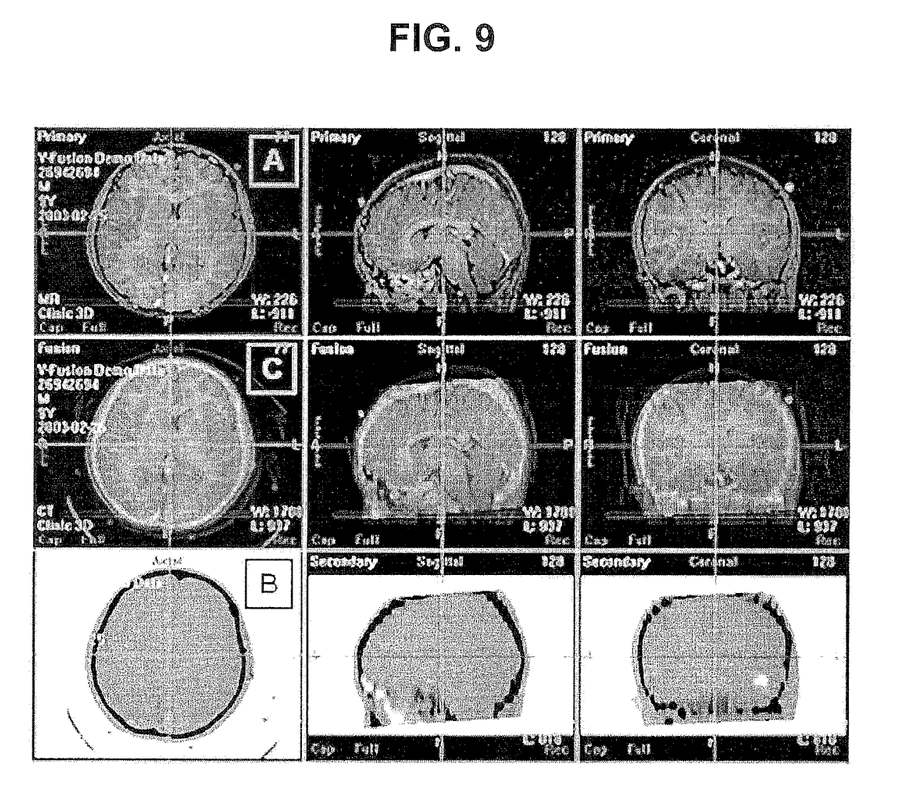
FIG. 9 is a view illustrating medical images before and after fusion.

As illustrated in FIG. 9, fusing medical image data A and B having different characteristics into one image C containing all the information is essential to efficiently make a medical diagnosis. One of the basic steps of the image fusion is to align postures of image volumes.

Figure 10:
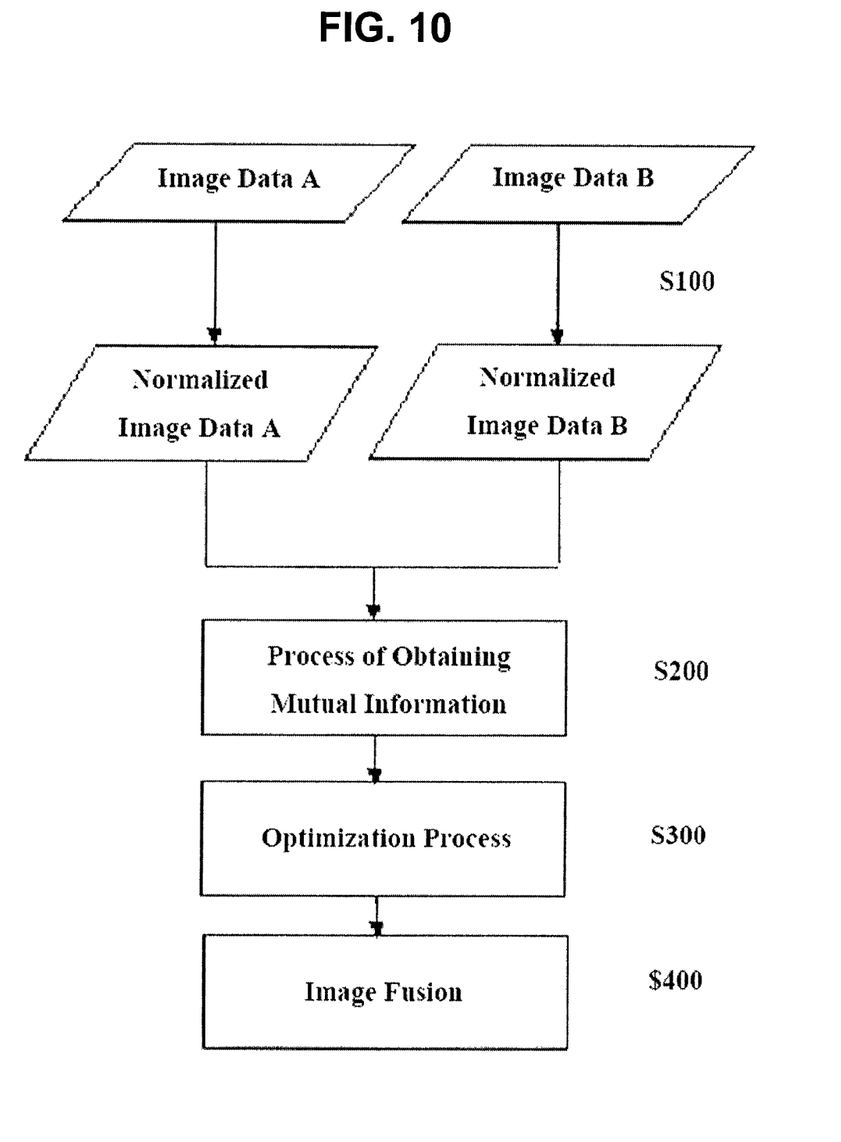
FIG. 10 is an explanatory view illustrating a process of fusing medical image data.

As shown in FIG. 10, a process of fusing medical image data includes a step S100 of normalizing two image data A and B having different characteristics, a step S200 of acquiring mutual information between the normalized image data A and B, an optimization step S300 of computing a linear transformation T maximizing the mutual information, and a step S400 of fusing the normalized image data A and B by means of the linear transformation T computed at step S300. Hereinafter, the step S300 of computing the linear transformation T maximizing the mutual information according to the present invention will be explained. The steps S100, S200 and S400 are well-known processes, and thus explanations thereof are omitted.

The aligning process, which is a previous step of the process of fusing two 3D medical image data A and B into one image data, aligns the positions and postures of the two 3D medical image data A and B on a 3D space. In the aligning process, the linear transformation T can be defined as follows:

$$T = \arg\max MI(T(A), B)$$

(Here, MI represents mutual information between the 3D medical image data A and B.)

The image alignment can be carried out by computing the linear transformation T maximizing the mutual information between the 3D medical image data, i.e., the volume data sets A and B.

In 1995, Viola firstly attempted to use mutual information that is a concept of an information theory for the 3D volume alignment. Since then, the mutual information has been widely used in the analysis of medical images such as CT and MRI. Explanations of a concrete method of maximizing mutual information are omitted. An aligning method disclosed in Korean Patent 10-0529119 by the present applicant can be a good example.

The invention claimed is:

1. A method of determining a position of a deep brain stimulation (DBS) electrode, the method locating the position of said DBS electrode with respect to a targeted region in a deep brain of a living subject, by using a first volume data set including information on said targeted region and a second volume data set including information on said DBS electrode implanted toward said targeted region, the method comprising the steps of:

generating a subvolume of said targeted region from said first volume data set, and also generating a subvolume of said DBS electrode from said second volume data set;

overlapping and displaying said subvolume of said targeted region and said subvolume of said DBS electrode to determine said position of said DBS electrode with respect to said targeted region, with said first volume data set and said second volume data set aligned; and determining the position of the DBS electrode with respect to said target region from viewing the overlapping of the subvolumes of said targeted region and said DBS electrode, wherein said first volume data set is acquired before the implantation of said DBS electrode, and said second volume data set is acquired after the implantation of said DBS electrode and, wherein said first volume data set is an MRI image and said second volume data set is a CT image.

2. The method of claim 1, wherein the alignment of said first volume data set with said second volume data set is carried out by means of mutual information between said first volume data set and said second volume data set.

3. The method of claim 1, comprising:
a step of reslicing said first volume data set on the basis of inter commissural anterior commissure (AC)-posterior commissural (PC) so as to improve identification of said targeted region, prior to the alignment.

4. The method of claim 3, comprising:
a step of reslicing said second volume data set on the basis of AC-PC so as to reduce an alignment time, prior to the alignment.

5. The method of claim 4, wherein the alignment is carried out by means of mutual information between said first volume data set and said second volume data set.

6. The method of claim 1, wherein said subvolume of said targeted region is generated from said first volume data set by means of an atlas.

7. The method of claim 1, wherein said targeted region is a subthalamic nucleus (STN).

8. A method of determining a position of a deep brain stimulation (DBS) electrode, comprising the steps of:

acquiring a first volume data set including information on a targeted region in a deep brain of a living subject and a second volume data set including information on said DBS electrode implanted toward said targeted region;

determining a correlation between said first volume data set and said second volume data set for alignment by means of mutual information;

extracting at least said targeted region from said first volume data set and extracting at least said DBS electrode from said second volume data set;

displaying said targeted region extracted from said first volume data set and said DBS electrode extracted from said second volume data set by using said correlation to determine said position of said DBS electrode with respect to said targeted region; and determining the position of the DBS electrode with respect to said targeted region from viewing said display, wherein said first volume data set is acquired before the implantation of said DBS electrode, and said second volume data set is acquired after the implantation of said DBS electrode and, wherein said first volume data set is acquired from an MRI image, and said second volume data set is acquired from a CT image.

* * * * *